United States Patent [19]

Sutthoff et al.

[11] 4,110,164

[45] Aug. 29, 1978

[54] AGGLOMERATED FIBROUS CELLULOSE

[75] Inventors: Robert F. Sutthoff; Robert V. MacAllister; Khaja Khaleeluddin, all of Clinton, Iowa

[73] Assignee: Standard Brands Incorporated, New York, N.Y.

[21] Appl. No.: 788,728

[22] Filed: Apr. 19, 1977

[51] Int. Cl.$^2$ ............................................. C07G 7/02
[52] U.S. Cl. ...................................... 195/63; 195/68; 260/17 R; 260/17.4 CL; 195/31 F
[58] Field of Search ............ 260/17.4, 17 R, 17.4 CL; 195/31 F, 63, 68, DIG. 11

[56] References Cited

U.S. PATENT DOCUMENTS

| 3,708,397 | 1/1973 | Sipos | 195/31 R |
|---|---|---|---|
| 3,788,945 | 1/1974 | Thompson et al. | 195/31 F |
| 3,823,133 | 7/1974 | Hurst et al. | 260/231 A |
| 3,838,007 | 9/1974 | van Velzen | 195/31 R |
| 3,909,354 | 9/1975 | Thompson et al. | 195/31 F |
| 3,947,325 | 3/1976 | Dinelli et al. | 195/68 |
| 3,956,065 | 5/1976 | Idaszak et al. | 195/31 F |
| 4,029,546 | 6/1977 | Brouillard | 195/31 R |
| 4,033,817 | 7/1977 | Gregor | 195/2 |

FOREIGN PATENT DOCUMENTS 910,202 11/1962 United Kingdom.

OTHER PUBLICATIONS

Peterson et al., J.A.C.S., vol. 78, pp. 751–755 (1956).
Guthrie et al., Industrial and Engineering Chemistry, vol. 52, pp. 935–937 (1960).
Tsumura et al., Nippon Shokuhim Kogyo Gakkaishi, vol. 14, No. 12, pp. 89–92, (1967).
Peska et al., Die Angewandte Makromolekulare Chemie, vol. 53, pp. 73–80, (1976).

Primary Examiner—Lionel M. Shapiro

[57] ABSTRACT

An agglomerated fibrous ion exchange cellulose composite wherein the cellulose is embedded in a hydrophobic polymer and relatively large portions of the cellulose are free to adsorb charged macro-molecules.

18 Claims, No Drawings

AGGLOMERATED FIBROUS CELLULOSE

BACKGROUND OF THE INVENTION

1. Field of the Invention

The present invention is directed to an agglomerated fibrous ion exchange cellulose composite which will effectively adsorb and immobilize enzymes.

More particularly, the present invention is directed to an agglomerated fibrous ion exchange cellulose composite containing glucose isomerase which exhibits improved porosity characteristics.

2. Description of the Prior Art

Early processes for preparing fructose containing solutions whereby glucose was converted to fructose in the presence of alkaline catalysts or sucrose was inverted to glucose and fructose by means of acid have been largely superseded by enzymatic methods. The present commercial methods involve the isomerization of glucose to fructose by glucose isomerase elaborated by various genera of microorganisms.

Because of the economics involved in producing glucose isomerase, it is of the utmost importance to use the isomerase under conditions whereby maximum yields of fructose are produced using minimum quantities of glucose isomerase. Moreover, the conditions for isomerization should be such that minimal quantities of objectionable by-products are produced.

In recent years, more economical methods for producing fructose containing solutions have been developed utilizing glucose isomerase bound or immobilized on inert support materials. Such materials include various polymeric substances such as derivatized cellulose, ion exchange resins and synthetic fibers, glass, insoluble organic and inorganic compounds, etc. Glucose isomerase has also been encapsulated or englobed in suitable materials but such preparations suffer from the disadvantage that they generally cannot be reused.

Cellulose occurs in nature as a linear polymer comprised of anhydroglucose units joined together by $\beta$-1,4 glucosidic bonds. Each anhydroglucose unit contains three free hydroxyl groups capable of reacting with appropriate reagents to form insoluble cellulose derivatives which, due to their relative inertness, large surface area and open, porous structure, have a high adsorptive or ion-exchange capacity for protein molecules.

The preparation and utilization of ion exchange enzyme adsorbents derived from cellulose are known in the art. Peterson and Sober, *J.A.C.S.*, 78, 751 (1956) and Guthrie and Bullock, I/EC, 52, 935 (1960) described methods for preparing adsorptive cellulose products which could be utilized to separate or purify enzymes and other proteins. Tsumura et al., *Nippon Shokuhin Kogyo Gakkaishi*, 14, (12), (1967) disclosed binding glucose isomerase to DEAE Sephadex.

U.S. Pat. No. 3,708,397 to Sipos relates to a process for immobilizing glucose isomerase on basic anion exchange celluloses. U.S. Pat. No. 3,823,133 to Hurst et al. is directed to a method for preparing cationic cellulose ethers having a high adsorptive capacity for enzyme and other proteinaceous materials. U.S. Pat. No. 3,838,007 to van Velzen sets forth a process in which an enzyme preparation is obtained in particulate form. U.S. Pat. Nos. 3,788,945 and 3,909,354, both to Thompson et al., disclose continuous processes for converting glucose to fructose by passing a glucose-containing solution through fixed or fluidized beds containing glucose isomerase bound to various cellulose products. U.S. Pat. No. 3,947,325 to Dinelli et al. is directed to the preparation of cellulose containing englobed enzymatic material. The cellulose is formed from an emulsion comprising an aqueous enzyme solution and nitrocellulose. U.S. Pat. No. 3,956,065 to Idaszak et al. is concerned with a continuous process for converting glucose to fructose whereby a glucose containing solution is passed through a bed comprising a cellulose derivative having glucose isomerase immobilized thereon and non-porous or granular polystyrene beads. The beads inhibit packing and channeling of the bed when such is used in flow reactors. Peska et al. in an article entitled "Ion Exchange Derivatives of Bead Cellulose," *Die Angewandte Makromolekulare Chemie*, 53, pp. 73–80 (1976), describes several derivatized celluloses prepared in bead form.

OBJECTS OF THE INVENTION

It is a principal object of the present invention to provide an agglomerated fibrous ion exchange cellulose preparation capable of adsorbing and immobilizing charged macro-molecules.

It is another object to provide an agglomerated fibrous ion exchange cellulose preparation having enhanced porosity in respect to the flow of a solution of a substrate when such preparation is used as an immobilized enzyme support.

These and other objects of the invention will be apparent from the present specification and the appended claims.

SUMMARY OF THE INVENTION

An agglomerated fibrous ion exchange cellulose composite wherein the cellulose is embedded in a hydrophobic polymer and relatively large portions of the cellulose are free to adsorb charged macro-molecules.

DETAILED DESCRIPTION OF THE INVENTION

While the following description and Examples are primarily directed to the utilization of agglomerated fibrous ion exchange cellulose to adsorb and immobilize glucose isomerase, it is contemplated that the agglomerated material will have the capability of adsorbing charged macro-molecules such as proteins, nucleic acids and the like, and, further, would be capable of recovery of said molecules from a variety of substances such as food waste streams, e.g. recovery of protein from milk whey, meat processing streams and vegetable processing streams, reduction of BOD from waste streams, etc.

Fibrous ion exchange cellulose has extremely high loading capacities in regard to binding or immobilizing enzymes, especially glucose isomerase. In general, the fibrous cellulose materials determined most useful in practicing the present invention can be characterized as anion-exchange celluloses. Exemplary of such materials are the di- and tri-ethylaminoethyl celluloses, such as DEAE-cellulose and TEAE-cellulose, and the cellulose derivatives of epichlorohydrin and triethanolamine, such as ECTEOLA-cellulose.

The term "fibrous" as used in this specification and the appended claims refers to cellulose derived from natural sources which has been subdivided or fiberized by mechanical or chemical means and does not include cellulose or derivatives thereof which have been subjected to chemical treatments which result in dissolution of the natural fibrous structure of the cellulose such as may occur when cellulose is derivatized to certain degrees of substitution.

Due to the high loading capacity of fibrous ion exchange cellulose preparations containing glucose isomerase, when such are utilized in industrial applications only relatively small reactors are necessary to convert large quantities of glucose to fructose.

Additionally, because of this high loading capacity, the substrate and the resulting product are maintained under isomerization conditions for only a short period. These isomerization conditions, generally, are conductive to production of small amounts of unwanted by-products due to the reactive nature of the fructose, and, thus, the longer the period the fructose is maintained under such conditions, the greater the amounts of unwanted by-products produced. Thus, the high loading capacity of fibrous ion exchange cellulose results in the substrate being isomerized to the desired degree in a short time, thereby decreasing the period during which the fructose component is maintained under isomerization conditions. However, such preparations containing fibrous ion exchange cellulose suffer from the disadvantage of "packing" and, therefore, such are usually utilized in shallow beds to avoid the development of problems due to excessive backpressure. Even when shallow beds are utilized, there is the possibility of channeling occurring whereby the substrate is not contacted to the desired degree with the bound or immobilized glucose isomerase. While certain immobilized glucose isomerase preparations have been developed to minimize these problems, they generally suffer other disadvantages, e.g., their capacity or glucose isomerase activity per unit volume is not as high as is desired, and/or they are not as economical as fibrous cellulose.

We have surprisingly discovered that when fibrous ion exchange cellulose is agglomerated with a hydrophobic polymer, such cellulose retains its capacity to immobilize or bind glucose isomerase.

A number of polymers may be utilized in agglomerating the fibrous ion exchange cellulose. Exemplary of such are melamine formaldehyde resins, epoxy resins, polystyrene and the like. The preferred polymer is polystyrene.

The agglomerated fibrous ion exchange cellulose composites of this invention also have the surprising property of being regenerated; that is, after the activity of the immobilized glucose isomerase has decreased to a certain extent due to denaturation or other factors resulting from prolonged use, a solution of solubilized glucose isomerase can be brought into contact with the bed or column of agglomerated cellulose so that the glucose isomerase activity thereof is increased again to the desired degree. Prior to regeneration, however, it is generally preferred to treat the composite with a solution of alkali to more readily make the ion exchange sites of the fibrous cellulose more available to isomerase adsorption. While we do not wish to be bound to any theory in regard to the mechanism involved, it is likely that substrate debris, denatured isomerase or other proteinaceous materials which have been attracted to the fibrous cellulose is removed or solubilized.

The agglomerated fibrous ion exchange cellulose composites do not suffer from serious packing problems and, therefore, can be utilized in deep bed reactors without difficulty. Moreover, the problem of channeling of the substrate is minimized.

Depending upon the specific gravity of the substrate, the agglomerated fibrous ion exchange cellulose composite may tend to float thereon and, therefore, there is the possibility of some loss of composite occurring through the inlet or outlet portions of column type reactors. Moreover, problems could occur when the column is initially packed with the composite. Therefore, in certain cases, it is additionally preferred to incorporate a densification agent into the agglomerated fibrous ion exchange cellulose composite to increase the density thereof.

While a variety of densification agents may be utilized, they must, of course, be substantially inert in regard to the substrate and also must not inactivate the glucose isomerase. Densification agents such as powdered metal oxide or silicates may be utilized.

To form the agglomerated fibrous composite, the fibrous cellulose must be embedded in the hydrophobic polymer in such a manner that the cellulose is not completely encapsulated or enrobed in the polymer. Otherwise, the capacity of the fibrous ion exchange cellulose to adsorb enzymes would be substantially deleteriously affected. The greater the free surface of the cellulose the greater the adsorptive capacity of the composite.

While a number of methods may be utilized to embed the fibrous cellulose in the hydrophobic polymer, the two which may be typically used involve dissolving the hydrophobic polymer and incorporating the other materials therein or heating the polymer to a plastic state and incorporating the other materials. The latter procedure is preferred since no solvent evaporation is necessary. The resulting material can then be reduced by grinding or the like and the granules classified on appropriate sized screens.

The particle size distribution of the granules may vary somewhat widely. Satisfactory results have been obtained using granules which passed through No. 20 and were retained on No. 50 U.S mesh screens.

In order to more clearly describe the nature of the present invention, specific examples will hereinafter be described. It should be understood, however, that this is done solely by way of example and is intended neither to delineate the scope of the invention nor limit the ambit of the appended claims.

EXAMPLE I

This Example illustrates the preparation of a DEAE-cellulose agglomerate not having a densification agent present and the utilization of the agglomerate in a continuous process for isomerizing glucose to fructose.

20 g of DEAE-cellulose (The cellulose derivative in this and the following examples were prepared in accordance with the method described in U.S. Pat. No. 3,823,133.) having an ion exchange capacity of 0.8 meq. per gram and 40 g of ground polystyrene were added with stirring to 60 ml of methylene chloride at ambient temperature into a viscous, homogeneous slurry. The slurry was spread onto a tray which was placed in a hood for about 18 hours until the methylene chloride had evaporated. The brittle, dried agglomerate was ground through a No. 20 U.S. mesh screen. Fines passing a 40 U.S. mesh screen were discarded.

36.8 g of the agglomerate granules was slurried in 60 ml of a solution of solubilized glucose isomerase containing 24 IGIU/ml and the slurry stirred for 80 minutes at ambient temperature and a pH of 7 following which the slurry was filtered. The granules adsorbed 338 IGIU/g, dry basis. 40 g of the wet glucose isomerase-DEAE-cellulose agglomerate preparation containing 8795 IGIU were slurried in a 50 percent by weight dextrose solution, 0.005 molar in MgSO$_4$ and 0.005 molar in NaHSO$_3$. The pH of the solution was 7.8 at 25° C. The granules with glucose isomerase immobilized thereon were added to a jacketed glass column 1.5 cm in diameter to a height of 47.7 cm. with the temperature of the system maintained at 65° C., a 50 percent, by weight, glucose solution having a viscosity of about 3 centipoise was passed in a continuous manner through the bed of granules at a flow rate of 1.8 ml per minute. The isomerized solution contained 47 percent fructose.

The initial pressure drop coefficient (K) of the column was determined to be 0.19 g min cm$^{-1}$ ml$^{-1}$ cps$^{-1}$. After 597 hours of continuous use, the pressure drop coefficient was determined to be 0.25 g min cm$^{-1}$ ml$^{-1}$ cps$^{-1}$. Since the pressure drop coefficient of the untreated fibrous DEAE-cellulose was 20 g min cm$^{-1}$ ml$^{-1}$ cps$^{-1}$, an approximately 100-fold decrease in pressure drop coefficient was effected by the process of the present invention. The pressure drop coefficient is defined as:

$$K = \Delta P/\mu V L$$

$K$ = pressure drop coefficient (g min cm$^{-1}$ ml$^{-1}$ cps$^{-1}$)
$\Delta P$ = pressure drop across the column (g/cm$^2$)
$\mu$ = viscosity of substrate (cps)
$V$ = flow rate through the column per cm$^2$ of bed area cross section (ml/min/cm$^2$)
$L$ = enzyme bed depth (cm)

EXAMPLE II

This Example illustrates the preparation of a DEAE-cellulose-polystyrene-alumina composite which has been formed by heating the polymer to a plastic state.

The following materials were used to form the composite:

265 g Polystyrene (Polysar-510 high impact polystyrene manufactured by Polysar-Plastics, Inc., High Ridge Park, Stamford, Conn.)

4.5 g aluminum stearate (utilized as a lubricant)

115 g fibrous DEAE-cellulose prepared by derivatizing C-100 chemical cellulose (International Filler Corp., North Tonawanda, NY) with diethylaminoethyl chloride hydrochloride. The ion-exchange capacity of the DEAE-cellulose was approximately 0.9 meq g$^{-1}$.

120 g alumina 10 $\mu$ (manufactured by Georgia Talc Co., Chatsworth, GA)

The polystyrene was heated to a plastic state and the aforementioned ingredients mixed therein. The mixture was passed between the rolls of a two-roll heated mill. The rolls were 12 inches long and 6 inches in diameter and one roll was heated to about 180° C.

The sheeted material was cooled, broken, ground in a Burr mill and screened to obtain a composite of 30 to 50 mesh granules using U.S. Standard Sieves. The fines were discarded.

Twelve grams of the granules were added to a 196 ml solution of glucose isomerase containing approximately 20 IGIU ml$^{-1}$ and buffered to a pH of 7.2. The suspension was stirred at 25° C. for 7 hours. The granules were separated by filtration, washed and the filtrate assayed for glucose isomerase activity. The granules adsorbed 330 IGIU g$^{-1}$ d.b. from solution by difference.

3.24 g of the immobilized granular enzyme was placed in a jacketed glass column 2.54 cm in diameter maintained at 65° C. and a 50% dextrose solution was passed through the bed of granules in a continuous manner at a flow rate of 0.52 ml/min. The isomerized solution contained 33.1% fructose.

The pressure drop coefficient (K) of the granular immobilized enzyme was determined for column operation in the following manner. About 185 g dry basis of the enzyme granules were added to a stainless steel column about 5 cm in diameter to a height of 22.9 cm. The column was maintained at a temperature of 50° C. A syrup containing 42% fructose and 50% dextrose at 70% d.s., pH of 7.8, and 50° C. was passed through the column at pressures of about 394, 703, 1758, and 4218 g/cm$^2$ for 2 hours at each pressure. The flow rate and pressure drop were recorded at 30 to 40 minute intervals.

The pressure drop coefficient of the packed column was determined to be 0.23 g min cm$^{-1}$ ml$^{-1}$ cps$^{-1}$ at 394 g/cm$^2$ and 0.35 g min cm$^{-1}$ ml$^{-1}$ cps$^{-1}$ at 4218 g/cm$^2$ after two hours running time at each experimental pressure.

The terms and expressions which have been employed are used as terms of description and not of limitation, and it is not intended in the use of such terms and expressions to exclude any equivalents of the features shown and described or portions thereof, since it is recognized that various modifications are possible within the scope of the invention claimed.

What is claimed is:

1. An agglomerated fibrous ion exchange cellulose composite wherein the cellulose is embedded in a hydrophobic polymer and relatively large portions of the cellulose have enzymes adsorbed thereon.

2. An agglomerated fibrous cellulose composite as defined in claim 1, wherein the fibrous cellulose possesses anion-exchange properties.

3. An agglomerated fibrous cellulose composite as defined in claim 2, wherein the hydrophobic polymer is polystyrene.

4. An agglomerated fibrous cellulose composite as defined in claim 3, wherein the composite contains a densification agent.

5. An agglomerated fibrous cellulose composite as defined in claim 3, wherein the densification agent is selected from the group consisting powdered metal oxides, silicates and mixtures thereof.

6. An agglomerated fibrous cellulose composite as defined in claim 2, wherein glucose isomerase is adsorbed on the fibrous anion exchange cellulose.

7. An agglomerated fibrous cellulose composite as defined in claim 6, wherein the anion exchange cellulose is DEAE-cellulose.

8. A method for preparing an agglomerated fibrous ion exchange cellulose composite having enzymes adsorbed thereon comprising forming a solution of a hydrophobic polymer and an organic solvent, mixing with the solution of the hydrophobic polymer fibrous ion exchange cellulose, removing the solvent from said mixture, forming an agglomerated composite therefrom and adsorbing enzymes on at least a portion of the cellulose of said composite.

9. A method for preparing an agglomerated fibrous ion exchange cellulose composite as defined in claim 8, wherein the hydrophobic polymer is polystyrene.

10. A method for preparing an agglomerated fibrous ion exchange cellulose composite having enzymes adsorbed thereon comprising heating a hydrophobic polymer to a plastic state, mixing therewith fibrous ion exchange cellulose, forming an agglomerated composite from the mixture and adsorbing enzymes on at least a portion of the cellulose of said composite.

11. A method for preparing an agglomerated fibrous ion exchange cellulose composite as defined in claim 10, wherein the hydrophobic polymer is polystyrene.

12. An agglomerated fibrous ion exchange cellulose composite as defined in claim 1, wherein the particle size of the composite is such that the composite will pass through a No. 20 U.S. mesh screen and be retained on a No. 50 U.S. mesh screen.

13. An agglomerated fibrous ion exchange cellulose composite as defined in claim 1, wherein the hydrophobic polymer is selected from the group consisting of malamine formaldehyde resins, epoxy resins, polystyrene and mixtures thereof.

14. A column or bed of agglomerates of a fibrous ion exchange cellulose composite wherein the cellulose is embedded in a hydrophobic polymer and relatively large portions of the cellulose have enzymes adsorbed thereon.

15. A column or bed of agglomerates of a fibrous ion exchange cellulose composite as defined in claim 14, wherein the fibrous cellulose possesses anion-exchange properties.

16. A column or bed of agglomerates of a fibrous ion exchange cellulose composite as defined in claim 15, wherein the hydrophobic polymer is polystyrene.

17. A column or bed of agglomerates of a fibrous ion exchange cellulose composite as defined in claim 16, wherein the composite contains a densification agent.

18. A column or bed of agglomerates of a fibrous ion exchange cellulose composite as defined in claim 15, wherein glucose isomerase is adsorbed on the fibrous anion exchange cellulose.

* * * * *